United States Patent

Cherpeck

[11] Patent Number: 5,538,521
[45] Date of Patent: Jul. 23, 1996

[54] FUEL COMPOSITIONS CONTAINING POLYALKYL AND POLY(OXYALKYLENE)AROMATIC ESTERS

[75] Inventor: Richard E. Cherpeck, Cotati, Calif.

[73] Assignee: Chevron Chemical Company, San Ramon, Calif.

[21] Appl. No.: 173,802

[22] Filed: Dec. 23, 1993

[51] Int. Cl.$^6$ ................ C10L 1/24; C10L 1/22; C10L 1/18
[52] U.S. Cl. ................ 44/389; 44/370; 44/384; 44/390; 44/391; 44/398; 44/400; 558/398; 558/399; 558/413; 558/414; 558/416; 560/8; 560/9; 560/11; 560/12; 560/14; 560/18; 560/37; 560/81
[58] Field of Search ................ 44/370, 384, 389, 44/390, 391, 398, 400; 558/398, 399, 413, 414, 416; 560/8, 9, 11, 12, 14, 18, 37, 81

[56] References Cited

U.S. PATENT DOCUMENTS

| | | | |
|---|---|---|---|
| 2,714,607 | 8/1955 | Matter | 260/471 |
| 3,005,828 | 10/1961 | Baldridge | 44/390 |
| 3,149,933 | 9/1964 | Ley et al. | 44/75 |
| 3,285,855 | 11/1966 | Dexter et al. | 252/57 |
| 3,434,814 | 3/1969 | Dubeck et al. | 44/69 |
| 3,457,286 | 7/1969 | Dexter et al. | 44/390 |
| 3,737,420 | 6/1973 | Brokmeier et al. | 260/85.5 R |
| 3,810,869 | 5/1974 | Zaweski | 44/390 |
| 3,849,085 | 11/1974 | Kreuz et al. | 44/78 |
| 3,920,729 | 11/1975 | Sagawa et al. | 44/391 |
| 4,134,846 | 1/1979 | Machleder et al. | 252/51.5 A |
| 4,231,759 | 11/1980 | Udelhofen et al. | 44/75 |
| 4,320,020 | 3/1982 | Lange | 252/51.5 R |
| 4,320,021 | 3/1982 | Lange | 252/51.5 R |
| 4,328,322 | 5/1982 | Baron | 521/163 |
| 4,347,148 | 8/1982 | Davis | 252/51.5 R |
| 4,386,939 | 6/1983 | Lange | 44/63 |
| 4,515,981 | 5/1985 | Otani et al. | 560/50 |
| 4,859,210 | 8/1989 | Franz et al. | 44/53 |
| 5,024,678 | 6/1991 | Mertens-Gottselig et al. | 44/400 |
| 5,039,775 | 8/1991 | Oyaizu | 528/68 |
| 5,081,295 | 1/1992 | Reardan et al. | 564/163 |
| 5,086,153 | 2/1992 | Oyaizu | 528/68 |
| 5,090,914 | 2/1992 | Reardan et al. | 435/188 |
| 5,103,039 | 4/1992 | Reardan et al. | 560/33 |
| 5,157,099 | 10/1992 | Reardan et al. | 528/68 |
| 5,192,325 | 3/1993 | Cherpeck | 44/387 |
| 5,196,142 | 3/1993 | Mollet et al. | 252/311 |
| 5,196,565 | 3/1993 | Ross | 560/55 |
| 5,211,721 | 5/1993 | Sung et al. | 44/389 |
| 5,366,519 | 11/1994 | Cherpeck | 44/389 |
| 5,441,544 | 8/1995 | Cherpeck | 44/384 |
| 5,462,567 | 12/1995 | Cherpeck | 44/347 |

OTHER PUBLICATIONS

CA 77:36190r, 1972.

*Primary Examiner*—Jerry D. Johnson
*Attorney, Agent, or Firm*—C. J. Caroli

[57] ABSTRACT

A fuel additive having the formula:

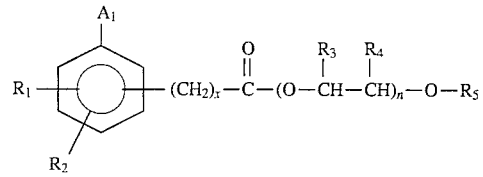

wherein $A_1$ is a thioether, a sulfoxide, a sulfone, a sulfonic acid, a sulfonamide, a nitrile, a carboxylic acid or ester, or a carboxamide; $R_1$ and $R_2$ are independently hydrogen, hydroxy, lower alkyl or lower alkoxy; $R_3$ and $R_4$ are independently hydrogen or lower alkyl; n is an integer from 0 to 100; and when n is 0 to 10, $R_5$ is polyalkyl having an average molecular weight of 450 to 5,000; and when n is 5 to 100, $R_5$ is hydrogen, alkyl, phenyl, aralkyl, alkaryl or an acyl group having the formula:

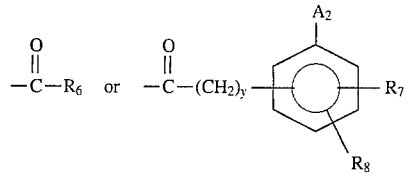

wherein $R_6$ is alkyl, phenyl, aralkyl or alkaryl; $R_7$ and $R_8$ are independently hydrogen, hydroxy, lower alkyl or lower alkoxy; $A_2$ is a thioether, a sulfoxide, a sulfone, a sulfonic acid, a sulfonamide, a nitrile, a carboxylic acid or ester, or a carboxamide; and x and y are independently integers from 0 to 10; with the proviso that when n and x are both 0, then $A_1$ may not be a carboxylic acid or ester, or a carboxamide.

66 Claims, No Drawings

5,538,521

FUEL COMPOSITIONS CONTAINING POLYALKYL AND POLY(OXYALKYLENE)AROMATIC ESTERS

BACKGROUND OF THE INVENTION

1. Field of the Invention

This invention relates to polyalkyl and poly(oxyalkylene) aromatic esters and to fuel compositions containing poly(oxyalkylene) aromatic esters. More particularly, this invention relates to polyalkyl and poly(oxyalkylene) aromatic esters which are substituted on the aromatic moiety and to the use of such compounds in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels. Similar amino phenols are disclosed in related U.S. Pat. No. 4,320,020, issued Mar. 16, 1982 to R. M. Lange.

Similarly, U.S. Pat. No 3,149,933, issued Sept. 22, 1964 to K. Ley et al., discloses hydrocarbon-substituted amino phenols as stabilizers for liquid fuels.

U.S. Pat. No 4,386,939, issued Jun. 7, 1983 to R. M. Lange, discloses nitrogen-containing compositions prepared by reacting an amino phenol with at least one 3- or 4-membered ring heterocyclic compound in which the hetero atom is a single oxygen, sulfur or nitrogen atom, such as ethylene oxide. The nitrogen-containing compositions of this patent are taught to be useful as additives for lubricants and fuels.

Nitro phenols have also been employed as fuel additives. For example, U.S. Pat. No 4,347,148, issued Aug. 31, 1982 to K. E. Davis, discloses nitro phenols containing at least one aliphatic substituent having at least about carbon atoms. The nitro phenols of this patent are taught to be useful as detergents, dispersants, antioxidants and demulsifiers for lubricating oil and fuel compositions.

Similarly, U.S. Pat. No 3,434,814, issued Mar. 25, 1969 to M. Dubeck et al., discloses a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy or halogen substituent.

More recently, certain poly(oxyalkylene) esters have been shown to reduce engine deposits when used in fuel compositions. U.S. Pat. No 5,211,721, issued May 18, 1993 to R. L. Sung et al., for example, discloses an oil soluble polyether additive comprising the reaction product of a polyether polyol with an acid represented by the formula RCOOH in which R is a hydrocarbyl radical having 6 to 27 carbon atoms. The poly(oxyalkylene) ester compounds of this patent are taught to be useful for inhibiting carbonaceous deposit formation, motor fuel hazing, and as ORI inhibitors when employed as soluble additives in motor fuel compositions.

Poly(oxyalkylene) esters of amino- and nitrobenzoic acids 15 are also known in the art. For example, U.S. Pat. No. 2,714,607, issued Aug. 2, 1955 to M. Matter, discloses polyethoxy esters of aminobenzoic acids, nitrobenzoic acids and other isocyclic acids. These polyethoxy esters are taught to have excellent pharmacological properties and to be useful as anesthetics, spasmolytics, analeptics and bacteriostatics. U.S. Pat. Nos. 2,714,608; 2,714,609; and 2,714,610, all issued to M. Matter, disclose similar polyethoxy esters.

Similarly, U.S. Pat. No 5,090,914, issued Feb. 25, 1992 to D. T. Reardan et al., discloses poly(oxyalkylene) aromatic compounds having an amino or hydrazinocarbonyl substituent on the aromatic moiety and an ester, amide, carbamate, urea or ether linking group between the aromatic moiety and the poly(oxyalkylene) moiety. These compounds are taught to be useful for modifying macromolecular species such as proteins and enzymes. U.S. Pat. Nos. 5,081,295; 5,103,039; and 5,157,099, all issued to D. T. Reardan et al., disclose similar poly(oxyalkylene) aromatic compounds.

U.S. Pat. No 4,328,322, issued Sept. 22, 1980 to R. C. Baron, discloses amino- and nitrobenzoate esters of oligomeric polyols, such as poly(ethylene) glycol. These materials are used in the production of synthetic polymers by reaction with a polyisocyanate. Similar materials are disclosed in U.S. Pat. No 4,515,981, issued May 7, 1985 to K. Otani et al., and in U.S. Pat. Nos. 5,039,775 and 5,086,153, both issued to Y. Oyaizu.

In addition, U.S. Pat. No 4,231,759, issued Nov. 4, 1980 to Udelhofen et al., discloses a fuel additive composition comprising the Mannich condensation product of (1) a high molecular weight alkyl-substituted hydroxyaromatic compound wherein the alkyl group has a number average molecular weight of about 600 to about 3,000, (2) an amine, and (3) an aldehyde. This patent teaches that such Mannich condensation products provide carburetor cleanliness when employed alone, and intake valve cleanliness when employed in combination with a hydrocarbon carrier fluid.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3,000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. No. 3,285,855, issued Nov. 15, 1966 to Dexter et al., discloses alkyl esters of dialkyl hydroxybenzoic and hydroxyphenylalkanoic acids wherein the ester moiety contains from 6 to 30 carbon atoms. This patent teaches that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross. U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

It has now been discovered that certain polyalkyl and poly(oxyalkylene) aromatic esters which are substituted on the aromatic moiety are surprisingly useful for reducing engine deposits, especially intake valve deposits, when employed as fuel additives in fuel compositions.

SUMMARY OF THE INVENTION

The present invention provides novel polyalkyl and poly(oxyalkylene) aromatic esters which are useful as fuel additives for the prevention and control of engine deposits, particularly intake valve deposits.

The polyalkyl and poly(oxyalkylene) aromatic esters of the present invention have the formula:

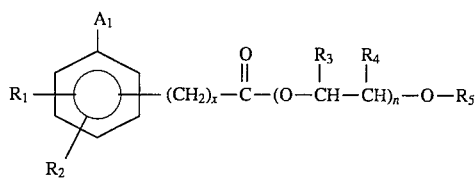

wherein $A_1$ is selected from the group consisting of $SR'$, $SOR''$, $SO_2R'''$, wherein $R'$, $R''$ and $R'''$ are independently lower alkyl of 1 to 6 carbon atoms; $SO_3H$; $SO_2NR^{IV}R^V$, wherein $R^{IV}$ and $R^V$ are independently hydrogen, lower alkyl of 1 to 6 carbon atoms or aminoalkyl of 1 to 6 carbon atoms, provided that $R^{IV}$ and $R^V$ may not both be aminoalkyl; CN; $CO_2R^{VI}$, wherein $R^{VI}$ is hydrogen or lower alkyl of 1 to 6 carbon atoms; and $C(O)NR^{VII}R^{VIII}$, wherein $R^{VII}$ and $R^{VIII}$ are independently hydrogen, lower alkyl of 1 to 6 carbon atoms or aminoalkyl of 1 to 6 carbon atoms, provided that $R^{VII}$ and $R^{VIII}$ may not both be aminoalkyl;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—CHRS$_3$—CHR$_4$— unit;

n is an integer from 0 to 100;

and when n is 0 to 10, then $R_5$ is a polyalkyl group having an average molecular weight in the range of about 450 to 5,000;

and when n is 5 to 100, then $R_5$ is hydrogen, alkyl having 1 to 100 carbon atoms, phenyl, aralkyl having 7 to 100 carbon atoms, alkaryl having 7 to 100 carbon atoms, or an acyl group having the formula:

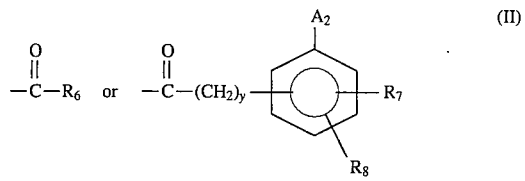

wherein $R_6$ is alkyl having 1 to 30 carbon atoms, phenyl, aralkyl having 7 to 36 carbon atoms or alkaryl having 7 to 36 carbon atoms;

$R_7$ and $R_8$ are independently hydrogen, hydroxy, lower alkyl having 1 to 6 carbon atoms, or lower alkoxy having 1 to 6 carbon atoms;

$A_2$ is selected from the group consisting of $SR^{IX}$, $SOR^X$, $SO_2R^{XI}$, wherein $R^{IX}$, $R^X$ and $R^{XI}$ are independently lower alkyl of 1 to 6 carbon atoms; $SO_3H$; $SO_2NR^{XII}R^{XIII}$, wherein $R^{XII}$ and $R^{XIII}$ are independently hydrogen or lower alkyl of 1 to 6 carbon atoms; CN; $CO_2R^{XIV}$, wherein $R^{XIV}$ is hydrogen or lower alkyl of 1 to 6 carbon atoms; and $C(O)NR^{XV}R^{XVI}$, wherein $R^{XV}$ and $R^{XVI}$ are independently hydrogen or lower alkyl of 1 to 6 carbon atoms;

and x and y are independently integers from 0 to 10;

with the proviso that when n and x are both 0, then $A_1$ may not be $CO_2R^{VI}$ or $C(O)NR^{VII}R^{VIII}$.

The present invention further provides a fuel composition comprising a major amount of hydrocarbons boiling in the gasoline or diesel range and an effective deposit-controlling amount of a polyalkyl or poly(oxyalkylene) aromatic ester of the present invention.

The present invention additionally provides a fuel concentrate comprising an inert stable oleophilic organic solvent boiling in the range of from about 150° F. (65° C.) to 400° F. (205° C.) and from about 10 to 70 weight percent of a polyalkyl or poly(oxyalkylene) aromatic ester of the present invention.

Among other factors, the present invention is based on the discovery that certain polyalkyl and poly(oxyalkylene) aromatic esters which are substituted on the aromatic moiety are surprisingly useful for reducing engine deposits, especially on intake valves, when employed as fuel additives in fuel compositions.

DETAILED DESCRIPTION OF THE INVENTION

The fuel additives provided by the present invention have the general formula:

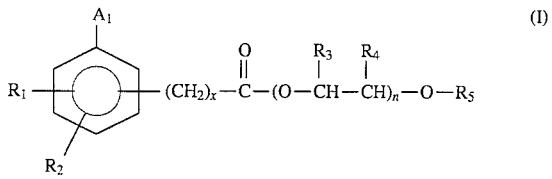

wherein $A_1$, $R_1$, $R_2$, $R_3$, $R_4$, $R_5$, n and x are as defined above.

In formula I, above, $A_1$ may be a thioether, $SR^I$, a sulfoxide $SOR^{II}$ a sulfone, $SO_2R^{III}$, a sulfonic acid, $SO_3H$, a sulfonamide, $SO_2NR^{IV}$, a nitrile(cyano), CN, a carboxylic acid or ester, $CO_2R^{VI}$, or a carboxamide, $C(O)NR^{VII}R^{VII}$.

Preferably, $A_1$ is a thioether, $SR^I$, a sulfone, $SO_2R^{III}$, a nitrile, CN, a carboxylic acid or ester, $CO_2R^{VI}$, or a carboxamide, $C(O)NR^{VII}R^{VII}$]. More preferably, $A_1$ is a carboxylic acid or a carboxylic acid ester, $CO_2R^{VI}$ or a carboxamide, $C(O)NR^{VII}R^{VIII}$.

Preferably, $R_1$ is hydrogen, hydroxy, or lower alkyl having 1 to 4 carbon atoms. More preferably, $R_1$ is hydrogen or hydroxy. Most preferably, $R_I$ is hydrogen.

$R_2$ is preferably hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

The number of oxyalkylene groups, n, may range from 0 to 100. When n ranges from 0 to about 10 oxyalkylene groups, then $R_5$ is a polyalkyl group having an average molecular weight in the range of about 450 to 5,000, preferably in the range of about 500 to 5,000, more preferably about 500 to 3,000, and most preferably about 600 to 2,000.

Moreover, when n ranges from about 5 to 100 oxyalkylene groups, $R_5$ is preferably hydrogen, alkyl having 1 to 30 carbon atoms, or alkylphenyl having an alkyl group containing 1 to 30 carbon atoms. More preferably, $R_5$ is hydrogen, alkyl having 2 to 24 carbon atoms, or alkylphenyl having an alkyl group containing 2 to 24 carbon atoms. Still more preferably, $R_5$ is hydrogen, alkyl having 4 to 12 carbon atoms or alkylphenyl having an alkyl group containing 4 to 12 carbon atoms. Most preferably, $R_5$ is alkylphenyl having an alkyl group containing 4 to 12 carbon atoms.

$R_6$ is preferably alkyl having 4 to 12 carbon atoms.

Preferably, $R_7$ is hydrogen, hydroxy, or lower alkyl having 1 to 4 carbon atoms. More preferably, $R_7$ is hydrogen or hydroxy. Most preferably, $R_7$ is hydrogen.

$R_8$ is preferably hydrogen.

Preferably, $A_2$ is a thioether, $SR^{IX}$, a sulfone, $SO_2R^{XI}$, a nitrile, CN, a carboxylic acid or ester, $CO_2R^{XIV}$, or a carboxamide, $C(O)NR^{XV}R^{XVI}$. More preferably, $A_2$ is a carboxylic acid or ester, $CO_2R^{XIV}$, or a carboxamide, $C(O)NR^{XV}R^{XVI}$.

As indicated above, n is an integer from 0 to 100. In one embodiment of the present invention, where $R_5$ is a polyalkyl group having an average molecular weight of 450 to 5,000, the number of oxyalkylene groups, n, will generally range from 0 to about 10, preferably from 0 to about 5, and more preferably, n will be 0.

In another embodiment of the present invention, where $R_5$ is hydrogen, alkyl of 1 to 100 carbon atoms, phenyl, aralkyl of 7 to 100 carbon atoms, alkaryl of 7 to 100 carbon atoms or an acyl group, the number of oxyalkylene groups, n, will generally range from about 5 to 100, preferably from about 8 to 50, and more preferably, n will be an integer from about 10 to 30.

Preferably, x will be an integer from 0 to 2. More preferably, x will be 0. Preferably, y will be an integer from 0 to 2. More preferably, y will be 0.

It is especially preferred that the $A_1$ substituent present in the aromatic moiety of the aromatic esters of this invention be situated in a meta or para position relative to the ester moiety. When the aromatic moiety also contains a hydroxyl substituent, it is particularly preferred that this hydroxyl group be in a meta or para position relative to the ester moiety and in an ortho position relative to the $A_1$ substituent.

The polyalkyl and poly(oxyalkylene) aromatic esters employed in the present invention will generally have a sufficient molecular weight so as to be non-volatile at normal engine intake valve operating temperatures (about 200°–250° C.). Typically, the molecular weight of the polyalkyl and poly(oxyalkylene) aromatic esters will range from about 600 to about 10,000, preferably from about 600 to 3,000.

Generally, the poly(oxyalkylene) aromatic esters employed in this invention will contain an average of about 5 to about 100 oxyalkylene units; preferably, 8 to 50 oxyalkylene units; more preferably, 10 to 30 oxyalkylene units.

Fuel-soluble salts of the polyalkyl and poly(oxyalkylene) aromatic esters of the present invention can be readily prepared for those compounds containing an amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein the following terms have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —$OR_d$ wherein $R_d$ is lower alkyl. Typical lower alkoxy groups include methoxy, ethoxy, and the like.

The term "alkaryl" refers to the group:

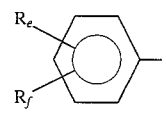

wherein $R_e$ and $R_f$ are each independently hydrogen or an alkyl group, with the proviso that both $R_e$ and $R_f$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_e$ is alkyl and $R_f$ is hydrogen.

The term "aralkyl" refers to the group:

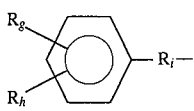

wherein $R_g$ and $R_h$ are each independently hydrogen or an alkyl group; and $R_i$ is an alkylene group. Typical alkaryl groups include, for example, benzyl, methylbenzyl, dimethylbenzyl, phenethyl, and the like.

The term "oxyalkylene unit" or "oxyalkylene group" refers to an ether moiety having the general formula:

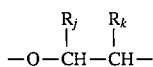

wherein $R_j$ and $R_k$ are each independently hydrogen or lower alkyl groups.

The term "poly(oxyalkylene)" refers to a polymer or oligomer having the general formula:

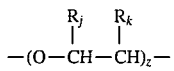

wherein $R_j$ and $R_k$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

General Synthetic Procedures

The polyalkyl and poly(oxyalkylene) aromatic esters employed in this invention can be prepared by the following general methods and procedures. Those skilled in the art will recognize that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but one skilled in the art will be able to determine such conditions by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxyl group, if present, will preferably be protected, when necessary, as the benzyl or tert-butyldimethylsilyl ether. Introduction and removal of these protecting groups is well described in the art.

The polyalkyl and poly(oxyalkylene) aromatic esters of the present invention having the formula:

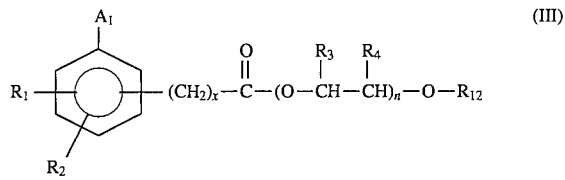

wherein $A_1$, $R_1$–$R_4$, n and x are as defined above and $R_{12}$ is an alkyl, phenyl, aralkyl, alkaryl or polyalkyl group, may be prepared by esterifying an aromatic carboxylic acid having the formula:

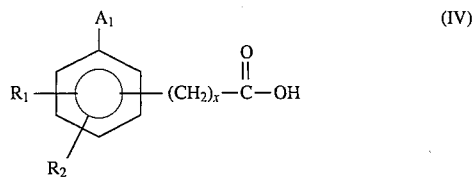

wherein $A_1$, $R_1$, $R_2$ and x are as defined above, with an alcohol having the formula:

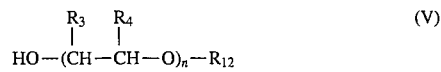

wherein n is 0 to 100 and $R_3$, $R_4$ and $R_{12}$ are as defined above, using conventional esterification reaction conditions.

This reaction is typically conducted by contacting the alcohol V with about 0.25 to about 1.5 molar equivalents of aromatic carboxylic acid IV in the presence of an acidic catalyst at a temperature in the range of 70° C. to about 160° C. for about 0.5 to about 48 hours. Suitable acid catalysts for this reaction include, for example, p-toluenesulfonic acid, methanesulfonic acid, sulfuric acid and the like. The reaction may be conducted in the presence or absence of an inert solvent, such as toluene, xylene and the like. The water generated during this reaction may be continuously removed by conventional procedures, such as azeotropic distillation with an inert solvent, such as xylene.

Alternatively, the polyalkyl and poly (oxyalkylene) aromatic esters of formula III may be prepared by reacting the alcohol V with an acid halide derived from aromatic carboxylic acid IV, such as an acid chloride or acid bromide.

Generally, the carboxylic acid moiety of IV may be converted into an acyl halide moiety by contacting IV with an inorganic acid halide, such as thionyl chloride, phosphorous trichloride, phosphorous tribromide, or phosphorous pentachloride; or with oxalyl chloride. Typically, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

Reaction of the acid halide derived from IV with the alcohol V provides a polyalkyl or poly(oxyalkylene) aromatic ester of formula III. Typically, this reaction is conducted by contacting alcohol V with about 0.25 to about 1.5 molar equivalents of the acid halide in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as triethylamine, di(isopropyl)ethylamine, pyridine or 4-dimethylaminopyridine.

The aromatic carboxylic acids of formula IV employed in the above-described procedures are either known compounds or can be prepared from known compounds by conventional procedures. Representative aromatic carboxylic acids suitable for use in these reactions include, for example, 4-methythiobenzoic acid, 4-methylsulfoxybenzoic acid, 4-methylsulfonylbenzoic acid, 4-cyanobenzoic acid, mono-methyl terephthalic acid, 4-carboxybenzenesulfonamide, 4-carboxybenzenesulfonic acid, and the like.

Preferred aromatic carboxylic acids include 4-methylthiobenzoic acid, 4-methylsulfonylbenzoic acid, 4-cyanobenzoic acid, and mono-methyl terephthalic acid.

Alternatively, substituent $A_1$ can be further modified by conventional procedures well known to those skilled in the art to provide additional aromatic compounds encompassed by formula III, above.

The alcohols of formula V, above, will include polyalkyl alcohols, $R_{12}OH$, where the number of oxyalkylene groups, n, is 0 and $R_{12}$ is polyalkyl.

The polyalkyl alcohols for formula V having no oxyalkylene groups may be prepared by conventional procedures known in the art. Such procedures are taught, for example, in U.S. Pat. Nos. 5,055,607 to Buckley and 4,859,210 to Franz et al., the disclosures of which are incorporated herein by reference.

In general, the polyalkyl substituent on the polyalkyl alcohols of formula V and the resulting polyalkyl aromatic esters of the present invention will have an average molecular weight in the range of about 450 to 5,000, preferably about 500 to 5,000, more preferably about 500 to 3,000, and most preferably about 600 to 2,000.

The polyalkyl substituent on the polyalkyl alcohols employed in the invention may be generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkyl alcohols are polyisobutenes which comprise at least about 20% of the more reactive methylvinylidene isomer, preferably at least 50%, and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain.

Examples of suitable polyisobutenes having a high alkylvinylidene content include Ultravis 30, a polyisobutene having a molecular weight of about 1300 and a methylvinylidene content of about 74%, and Ultravis 10, a polyisobutene having a molecular weight of about 950 and a methylvinylidene content of about 76%, both available from British Petroleum.

The polyalkyl alcohols may be prepared from the corresponding olefins by conventional procedures. Such procedures include hydration of the double bond to give an alcohol. Suitable procedures for preparing such long-chain alcohols are described in I. T. Harrison and S. Harrison, *Compendium of Organic Synthetic Methods*, Wiley-Interscience, New York (1971), pp. 119–122, as well as in U.S. Pat. Nos. 5,055,607 and 4,859,210.

The alcohols of formula V, above, will also include poly(oxyalkylene) alcohols, where the number of oxyalkylene units, n, is greater than 0, that is, from 1 to about 100.

The poly(oxyalkylene) alcohols of formula V are also known compounds that can be prepared using conventional procedures. For example, suitable procedures for preparing such compounds are taught in U.S. Pat. Nos. 2,782,240 and 2,841,479, the disclosures of which are incorporated herein by reference.

Preferably, the poly(oxyalkylene) alcohols of formula V are prepared by contacting an alkoxide or phenoxide metal salt having the formula:

$$R_{12}OM \qquad (VI)$$

wherein $R_{12}$ is as defined above and M is a metal cation, such as lithium, sodium, potassium and the like, with about 1 to about 100 molar equivalents of an alkylene oxide (an epoxide) having the formula:

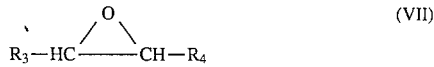

$$R_3-HC\overset{O}{\underset{}{\diagup\diagdown}}CH-R_4 \qquad (VII)$$

wherein $R_3$ and $R_4$ are as defined above.

Typically, metal salt VI is prepared by contacting the corresponding hydroxy compound $R_{12}OH$ with a strong base, such as sodium hydride, potassium hydride, sodium amide and the like, in an inert solvent, such as toluene, xylene and the like, under substantially anhydrous conditions at a temperature in the range from about $-10°$ C. to about $120°$ C. for about 0.25 to about 3 hours.

Metal salt VI is generally not isolated, but is reacted in situ with alkylene oxide VII to provide, after neutralization, the poly(oxyalkylene) alcohol V. This polymerization reaction is typically conducted in a substantially anhydrous inert solvent at a temperature of about $30°$ C. to about $150°$ C. for about 2 to about 120 hours. Suitable solvents for this reaction, include toluene, xylene and the like. Typically, the reaction is conducted at a pressure sufficient to contain the reactants and the solvent, preferably at atmospheric or ambient pressure.

The amount of alkylene oxide employed in this reaction will generally depend on the number of oxyalkylene units desired in the product. Typically, the molar ratio of alkylene oxide VII to metal salt VI will range from about 1:1 to 100:1, preferably from 5:1 to about 100:1, more preferably from 8:1 to 50:1, and most preferably from 10:1 to 30:1.

Alkylene oxides suitable for use in this polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g., propylene oxide, in which case the product is a homopolymer, e.g., a poly(oxypropylene) polymer. Copolymers are equally satisfactory and random copolymers can be prepared by contacting metal salt VI with a mixture of alkylene oxides, such as a mixture of propylene oxide and 1,2-butylene oxide, under polymerization conditions. Copolymers containing blocks of oxyalkylene units are also suitable for use in this invention. Block copolymers can be prepared by contacting metal salt VI with first one alkylene oxide, then others in any order, or repetitively, under polymerization conditions.

Poly(oxyalkylene) copolymers prepared by terminating or capping the poly(oxyalkylene) moiety with 1 to oxyethylene units, preferably 2 to 5 oxyethylene units, are particularly useful in the present invention, since these copolymers have been found to be more readily esterified than those having an alkyl branch in the terminal oxyalkylene unit. These copolymers may be prepared by contacting metal salt IV with an alkylene oxide of formula VII, such as 1,2-butylene oxide or propylene oxide, under polymerization conditions and then capping or terminating the resulting block of oxyalkylene units with oxyethylene units by adding ethylene oxide.

The poly(oxyalkylene) alcohol V may also be prepared by living or immortal polymerization as described by S. Inoue and T. Aida in *Encyclopedia of Polymer Science and Engineering*, Second Edition, Supplemental Volume, J. Wiley and Sons, New York, pages 412–420 (1989). These procedures are especially useful for preparing poly(oxyalkylene) alcohols of formula V in which $R_3$ and $R_4$ are both alkyl groups.

As noted above, the alkoxide or phenoxide metal salt VI used in the above procedures is generally derived from the corresponding hydroxy compound, $R_{12}OH$. Suitable hydroxy compounds include straight- or branched-chain aliphatic alcohols having 1 to about 100 carbon atoms and phenols having the formula:

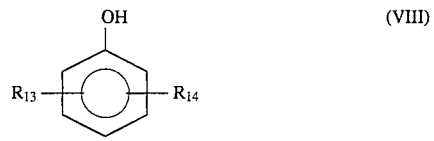

(VIII)

wherein $R_{13}$ is an alkyl group having 1 to about 100 carbon atoms and $R_{14}$ is hydrogen; or $R_{13}$ and $R_{14}$ are both alkyl groups, each independently containing 1 to about 50 carbon atoms.

Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octadecanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having 9 to about 100 carbon atoms and polybutylene alcohols having 12 to about 100 carbon atoms. Preferred straight- or branched-chain aliphatic alcohols will contain 1 to about 30 carbon atoms, more preferably 2 to about carbon atoms, and most preferably 4 to 12 carbon atoms. Particularly preferred aliphatic alcohols are butanols.

The phenols of formula VIII may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenol will contain 1 to about 30 carbon atoms, more preferably 2 to 24 carbon atoms, and most preferably 4 to 12 carbon atoms. Representative examples of phenols suitable for use in this invention include, but are not limited to, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$–$C_{18}$ alkylphenols, a mixture of $C_{18}$–$C_{24}$ alkylphenols, a mixture of $C_{20}$–$C_{24}$ alkylphenols, or a mixture of $C_{16}$–$C_{26}$ alkylphenols.

Particularly preferred alkylphenols are prepared by alkylating phenol with polymers or oligomers of $C_3$ to $C_6$ olefins, such as polypropylene or polybutene. These polymers typically contain 8 to about 100 carbon atoms, preferably 10 to 30 carbon atoms. An especially preferred alkylphenol is prepared by alkylating phenol with a propylene polymer having an average of four units. This polymer has the common name of propylene tetramer and is commercially available.

The poly(oxyalkylene) aromatic esters of formula I wherein $R_5$ is hydrogen, i.e., compounds having the formula:

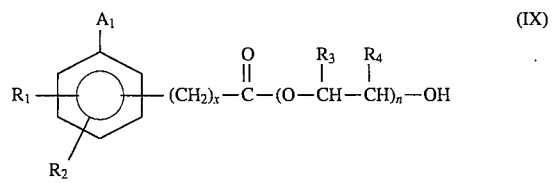

(IX)

wherein $A_1$, $R_1$–$R_4$, n and x are as defined above, may be prepared from compounds of formula III wherein $R_{12}$ is a labile hydrocarbyl group, such as a benzyl or t-butyl group, by removing the hydrocarbyl group under appropriate conditions to provide a hydroxyl group. For example, compounds of formula III where $R_{12}$ represents a benzyl group may be prepared by employing a metal salt VI derived from benzyl alcohol in the above-described synthetic procedures. Cleavage of the benzyl ether using conventional hydrogenolysis procedures then provides a compound of formula IX. Other labile hydrocarbyl groups, such as a t-butyl group, may be similarly employed for those compounds having functional groups that are not compatible with hydrogenolysis conditions, such as nitro groups. t-Butyl ethers may be cleaved under acidic conditions using, for example, trifluoroacetic acid.

The poly(oxyalkylene) aromatic esters of formula I wherein $R_5$ is an acyl group, i.e., compounds having the formula:

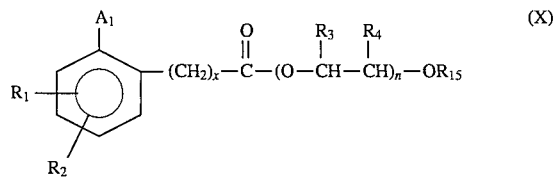

(X)

wherein $A_1$, $R_1$–$R_4$, n and x are as defined above and $R_{15}$ is an acyl group having the formula:

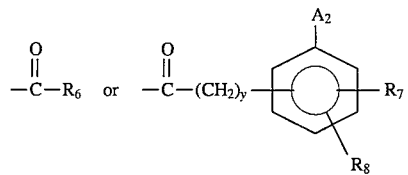

wherein $A_2$, $R_6$–$R_8$ and y are as defined above, may be synthesized from a compound of formula IX by acylating the terminal hydroxyl group of the poly(oxyalkylene) moiety with a suitable acylating agent.

Acylating agents suitable for use in this reaction include acid halides, such as acid chlorides and bromides; and carboxylic acid anhydrides. Preferred acylating agents include those having the formula: $R_6C(O)$—X, wherein $R_6$ is alkyl having 1 to 30, preferably 4 to 12 carbon atoms, phenyl, aralkyl having 7 to 36 carbon atoms or alkaryl having 7 to 36 carbon atoms, and X is chloro or bromo; and the acid halide derivatives of aromatic carboxylic acid IV described hereinabove.

Representative examples of preferred acylating agents having the formula $R_6C(O)—X$ include acetyl chloride, propionyl chloride, butanoyl chloride, pivaloyl chloride, octanoyl chloride, decanoyl chloride and the like.

Typically, acylation of IX is conducted by contacting IX with about 0.95 to about 1.2 molar equivalents of the acylating agent in an inert solvent, such as toluene, dichloromethane, diethyl ether and the like, at a temperature in the range of about 25° C. to about 150° C. for about 0.5 to about 48 hours. When an acid halide is employed as the acylating agent, the reaction is preferably conducted in the presence of a sufficient amount of an amine capable of neutralizing the acid generated during the reaction, such as triethylamine, di(isopropyl)ethylamine, pyridine or 4-dimethylamino pyridine.

A preferred group of poly(oxyalkylene) aromatic esters of formula X are those having the same aromatic ester group at each end of the poly(oxyalkylene) moiety, i.e., compounds of formula X wherein $R_{15}$ is an acyl group having the formula:

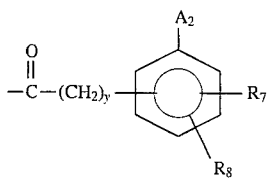

wherein $A_2=A_1$; $R_7=R_1$; $R_8=R_2$; and x and y are the same integer.

These compounds may be prepared from a poly(oxyalkylene) diol having the formula:

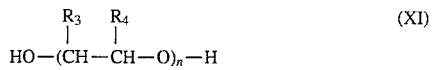  (XI)

wherein $R_3$, $R_4$, and n are as defined above, by esterifying each of the hydroxyl groups present in XI with a aromatic carboxylic acid of formula IV or an acyl halide derivative thereof using the above-described synthetic procedures. The poly(oxyalkylene) diols of formula XI are commercially available or may be prepared by conventional procedures, for example, by using sodium or potassium hydroxide in place of the alkoxide or phenoxide metal salt VI in the above-described alkylene oxide polymerization reaction.

Fuel Compositions

The polyalkyl and poly(oxyalkylene) aromatic esters of the present invention are useful as additives in hydrocarbon fuels to prevent and control engine deposits, particularly intake valve deposits. Typically, the desired deposit control is achieved by operating an internal combustion engine with a fuel composition containing a polyalkyl or poly(oxyalkylene) aromatic ester of the present invention. The proper concentration of additive necessary to achieve the desired level of deposit control varies depending upon the type of fuel employed, the type of engine, and the presence of other fuel additives.

In general, the concentration of the polyalkyl and poly(oxyalkylene) aromatic esters of this invention in hydrocarbon fuel will range from about 50 to about 2500 parts per million (ppm) by weight, preferably from 75 to 1,000 ppm. When other deposit control additives are present, a lesser amount of the present additive may be used.

The polyalkyl and poly(oxyalkylene) aromatic esters of the present invention may also be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the polyalkyl and poly(oxyalkylene) aromatic esters of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a polyalkyl or poly(oxyalkylene) aromatic ester of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present. invention and synthetic preparations thereof; and therefore these examples should not be interpreted as limitations upon the scope of this invention.

Example 1

Preparation of 4-Methylthiobenzoyl Chloride

To a flask equipped with a magnetic stirrer and a drying tube was added 10.0 grams of 4-methylthiobenzoic acid, 150 mL of anhydrous dichloromethane, and then 13 mL of oxalyl chloride. The resulting mixture was stirred at room temperature for 16 hours and then the solvents removed in vacuo to yield 13.1 grams of the desired acid chloride as an orange yellow solid.

EXample 2

Preparation of 4-Methylsulfonylbenzoyl chloride

To a flask equipped with a magnetic stirrer and a drying tube was added 10.0 grams of 4-methylsulfonylbenzoic acid, 150 mL of anhydrous dichloromethane, and then 10.9 mL of oxalyl chloride. 1 mL of anhydrous N,N-dimethylformamide was then added. The resulting mixture was stirred at room temperature for 16 hours and then the solvents removed in vacuo to yield 12.8 grams of the desired acid chloride as a light yellow solid.

Example 3

Preparation of α-(4-Methylthiobenzoyl)-ω-4-dodecylphenoxypoly (oxybutylene)

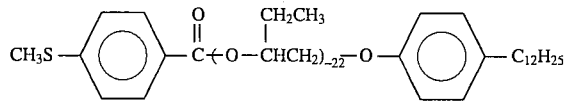

4-Methylthiobenzoyl chloride (13.1 grams, from Example 1) was combined with 123.3 grams of α-hydroxy-ω-4 dodecylphenoxypoly(oxybutylene) having an average of 22 oxybutylene units (prepared essentially as described in Example 6 of U.S. Pat. No. 4,160,648) and 500 mL of anhydrous toluene. Triethylamine (9.8 mL) and 4-dimethylamino pyridine (4.08 grams) were then added and the resulting mixture was heated to reflux under nitrogen for 16 hours. The reaction was cooled to room temperature and diluted with 1 liter of diethyl ether. The organic layer was then washed with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 122.1 grams of the desired product as a brown oil. The oil was chromatographed on silica gel, eluting with hexane/ethyl acetate/ethanol (90:8:2) to afford 60.0 grams of the desired product as a yellow oil. The product had an average of 22 oxybutylene units. $^1$H NMR (CDCl$_3$) δ7.95, 7.3(AB quartet, 4H), 7.1–7.3 (m, 2H), 6.75–6.95 (m, 2H), 5.05–5.2 (m, 1H), 3.85–4.0 (m, 2H), 3.1–3.85 (m, 63H), 2.5 (s, 3H), 0.6–1.8 (m, 135H).

Example 4

Preparation of α-(4-methylsulfonylbenzoyl-ω-4-dodecylphenoxypoly (oxybutylene)

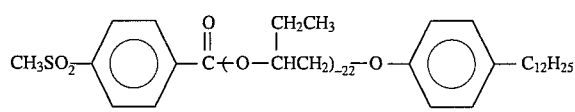

4-Methylsulfonylbenzoyl chloride (12.8 grams, from Example 2) was combined with 98.2 grams of α-hydroxy-ω-4 -dodecylphenoxypoly(oxybutylene) having an average of 22 oxybutylene units (prepared essentially as described in Example 6 of U.S. Pat. No. 4,160,648) and 500 mL of anhydrous toluene. Triethylamine (7.8 mL) and 4-dimethylamino pyridine (3.24 grams) were then added and the resulting mixture was heated to reflux under nitrogen for 16 hours. The reaction was cooled to room temperature and diluted with I liter of diethyl ether. The organic layer was then washed with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 101.6 grams of the desired product as a yellow oil. The oil was chromatographed on silica gel, eluting with hexane/ethyl acetate/ethanol (90:8:2) to afford 73.8 grams of the desired product as a yellow oil. The product had an average of 22 oxybutylene units. $^1$H NMR (CDCl$_3$) δ8.25, 8.0 (AB quartet, 4H), 7.1–7.3 (m, 2H), 6.75–6.95 (m, 2H), 5.1–5.3 (m, 1H), 3.85–4.0 (m, 2H), 3.1–3.85 (m, 63H), 3.1 (s, 3H), 0.6–1.8 (m, 135H).

Example 5

Preparation of Polyisobutyl -4-methylthiobenzoate

To a flask equipped with a mechanical stirrer, thermometer, Dean-Stark trap, reflux condensor and nitrogen inlet was added 35.0 grams of polyisobutanol (molecular weight average 984, prepared via hydroformylation of Amoco H-100 polyisobutene), 10.12 grams of 4-methylthiobenzoic acid and 0.86 grams of p-toluenesulfonic acid. The mixture was stirred at 130° C. for 16 hours, cooled to room temperature, and diluted with 500 mL of diethyl ether. The organic phase was washed twice with saturated aqueous sodium bicarbonate solution, and once with saturated aqueous sodium chloride. The organic layer was then dried over anhydrous magnesium sulfate, filtered and the solvents removed in vacuo to yield 34.2 grams of the desired product as a yellow oil. The oil was chromatographed on silica gel, eluting with hexane/ethyl acetate/ethanol (90:8:2) to afford 27.5 grams of the desired product as a yellow oil. IR (neat) 1722 cm$^{-1}$; $^1$H NMR (CDCl$_3$) δ7.85, 7.25 (AB quartet, 4H), 4.3 (t, 2H), 2.5 (s, 3H), 0.6–1.8 (m, 137H).

Example 6

Preparation of polyisobutyl-4-methylsulfonylbenzoate

To a flask equipped with a mechanical stirrer, thermometer, Dean-Stark trap, reflux condensor and nitrogen inlet was added 21.0 grams of polyisobutanol (molecular weight average 984, prepared via hydroformylation of Amoco H-100 polyisobutene), 7.23 grams of 4-methylsulfonylbenzoic acid and 0.52 grams of p-toluenesulfonic acid. The mixture was stirred at 130° C. for 16 hours, cooled to room temperature, and diluted with 500 mL of diethyl ether. The organic phase was washed twice with saturated aqueous sodium bicarbonate solution, and once with saturated aqueous sodium chloride. The organic layer was then dried over anhydrous magnesium sulfate, filtered and the solvents removed in vacuo to yield 14.5 grams of the desired product as a brown oil. The oil was chromatographed on silica gel, eluting with hexane/ethyl acetate/ethanol (90:8:2) to afford 8.7 grams of the desired product as a yellow oil. IR (neat) 1729 cm$^{-1}$; $^1$H NMR (CDCl$_3$) δ8.5, 8.1 (AB quartet, 4H), 4.35 (t, 2H), 3.1 (s, 3H), 0.6–1.8 (m, 137H).

Example 7

Preparation of
α-(4-Cyanobenzoyl)-ω-4-dodecylphenoxpoly
(oxybutylene)

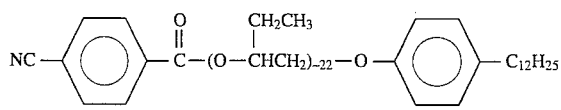

4-Cyanobenzoyl chloride (3.31 grams) was combined with 36.0 grams of α-hydroxy-ω-4-dodecylphenoxypoly(oxybutylene) having an average of 22 oxybutylene units (prepared essentially as described in Example 6 of U.S. Pat. No. 4,160,648) and 250 mL of anhydrous toluene. Triethylamine (3.9 mL) and 4-dimethylamino pyridine (1.5 grams) were then added and the resulting mixture was heated to reflux under nitrogen for 16 hours. The reaction was cooled to room temperature and diluted with 500 mL of hexane. The organic layer was then washed with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 44.5 grams of the desired product as a brown oil. The oil was chromatographed on silica gel, eluting with hexane/ethyl acetate/ethanol (70:25:5) to afford 22.0 grams of the desired product as a yellow oil. The product had an average of 22 oxybutylene units. IR (neat) 2233, 1722 cm$^{-1}$; $^1$H NMR (CDCl$_3$) δ8.2, 7.75 (AB quartet, 4H), 7.1–7.3 (m, 2H), 6.75–6.95 (m, 2H), 5.1–5.3 (m, 1H), 3.85–4.0 (m, 2H), 3.1–3.85 (m, 63H), 0.6–1.8 (m, 135H).

Exampble 8

Preparation of mono-Methyl terephthaloyl chloride

To a flask equipped with a magnetic stirrer, reflux condensor and nitrogen inlet was added 36.0 grams of mono-methyl terephthalic acid and 204.6 mL of thionyl chloride. The reaction was heated to reflux for 16 hours and the solvents removed in vacuo to yield 40.0 grams of the desired acid chloride as a white solid.

Example 9

Preparation of α-(4-Carbomethoxybenzoyl )
-ω-4-dodecylphenoxypoly(oxybutylene)

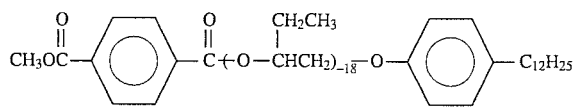

mono-Methyl terephthaloyl· chloride (40.0 grams, from Example 8) was combined with 359.0 grams of α-hydroxy-ω- 4-dodecylphenoxypoly(oxybutylene) having an average of 18 oxybutylene units (prepared essentially as described in Example 6 of U.S. Pat. No. 4,160,648) and 500 mL of anhydrous toluene. Triethylamine (30.7 mL) and 4-dimethylamino pyridine (12.2 grams) were then added and the resulting mixture was heated to reflux under nitrogen for 16 hours. The reaction was cooled to room temperature and diluted with 1.5 liters of hexane. The organic layer was then washed with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 400 grams of the desired product as a brown oil. The oil was chromatographed on silica gel, eldting with hexane/diethyl ether (1:1) to afford 220 grams of the desired product as a yellow oil. The product had an average of 18 oxybutylene units. IR (neat) 1722 cm$^{-1}$; $^1$H NMR (CDCl$_3$) δ8.1 (s, 4H), 7.1–7.3 (m, 2H), 6.75–6.95 (m, 2H), 5.1–5.25 (m, 1H), 3.85–4.0 (m, 2H), 3.8 (s, 3H), 3.1–3.85 (m, 51H), 0.6–1.8 (m, 115H).

Example 10

Preparation of
α-(4-Carboxybenzoyl)-ω-4-dodecyclphenoxypoly
(oxybutylene)

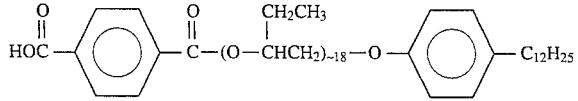

To a flask equipped with a magnetic stirrer and nitrogen inlet was added α-(4-carbomethoxybenzoyl)-ω-4-dodecylphenoxypoly(oxybutylene) (18 grams, from Example 9), 10% aqueous sodium hydroxide (w/w, 4.0 grams), and tetrahydrofuran (10 mL). The reaction was stirred at room temperature for 16 hours and the solvents removed in vacuo. The residue was diluted with 100 mL of water and acidified to pH 3 with concentrated hydrochloric acid. The aqueous layer was extracted three times with diethyl ether. The combined diethyl ether layers were dried over anhydrous magnesium sulfate, filtered and the solvents removed in vacuo to yield 13.8 grams as an oil. The oil was chromatographed on silica gel, eluting with hexane/diethyl ether (1:1), followed by hexane/diethyl ether/acetic acid (50:45:5) to afford 5.8 grams of the desired product. The product had an average of 18 oxybutylene units. IR (neat) 1722 cm$^{-1}$; $^1$H NMR (CDCl$_3$) δ8.05 (s, 4H), 7.0–7.2 (m, 2H), 6.7–6.9 (m, 2H), 5.1–5.25 (m, 1H), 3.85–4.0 (m, 2H), 3.1–3.85 (m, 51H), 0.6–1.8 (m, 115H).

Example 11

Preparation of
α-(mono-Terephthaloyl)-ω-4-dodecylphenoxypoly
(oxybutylene)chloride

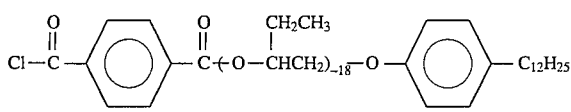

To a flask equipped with a magnetic stirrer and a drying tube was added 18.5 grams of α-(4-carboxybenzoyl)-ω-4-dodecylphenoxypoly(oxybutylene), 150 mL of anhydrous diethyl ether, and then 3 mL of oxalyl chloride. The resulting mixture was stirred at room temperature for 16 hours and then the solvents removed in vacuo to yield 18.5 grams of the desired acid chloride.

Example 12

Preparation of α-(4-Aminoethylcarbamylbenzoyl)
-ω-4-dodecylphenoxypoly(oxybutylene)

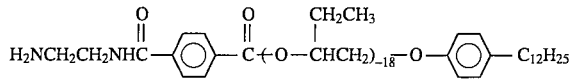

To a flask equipped with a magnetic stirrer, thermometer, addition funnel and nitrogen inlet was added ethylenediamine (4.4 mL) and 25 mL of diethyl ether. The contents of the flask were cooled to 0° C. and α-(mono-terephthaloyl)-ω-4-dodecylphenoxypoly(oxybutylene) chloride (18.5 grams, prepared as in Example 11) dissolved in 50 mL of diethyl ether was added dropwise. The reaction was stirred at room temperature for 16 hours, diluted with diethyl ether (200 mL), washed twice with saturated aqueous sodium bicarbonate solution, twice with water, and once with saturated aqueous sodium chloride. The organic layer was then dried over anhydrous magnesium sulfate, filtered and the solvents removed in vacuo to yield 22.6 grams of product. The oil was chromatographed on silica gel, eluting with hexane/diethyl ether/ethanol (70:29:1) to afford 6.5 grams of the desired product as an oil. The product had an average of 18 oxybutylene units. IH NMR (CDCl$_3$) δ8.1 (s, 4H), 7.1–7.3 (m, 2H), 6.75–6.95 (m, 2H), 5.1–5.25 (m, 1H), 3.85–4.0 (m, 2H), 3.1–3.85 (m, 53H), 2.5–2.7 (m, 2H), 0.6–1.8 (m, 115H).

Example 13

Preparation of
α-(4-Carbamylbenzoyl)-ω-4-dodecylphenoxypoly
(oxybutylene)

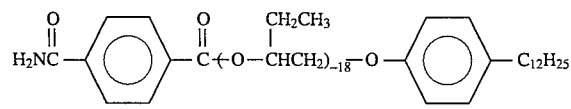

To a flask equipped with a magnetic stirrer, addition funnel and nitrogen inlet was added ammonia (12.5 mL of a 2.0M solution in methanol), dichloromethane (100 mL), and δ-(mono-terephthaloyl)-ω-4-dodecylphenoxypoly(oxybutylene) chloride (9.0 grams, prepared as in Example 11). The reaction was stirred at room temperature for 16 hours, diluted with dichloromethane (200 mL), washed twice with saturated aqueous sodium bicarbonate solution, and once with saturated aqueous sodium chloride. The organic layer was then dried over anhydrous magnesium sulfate, filtered and the solvents removed in vacuo to yield 7.1 grams of the desired product as a brown oil. The product had an average of 18 oxybutylene units. IR (neat) 1722, 1682 cm$^{-1}$; $^1$H NMR (CDCl$_3$) δ8.1, 7.8 (AB quartet, 4H), 7.1–7.3 (m, 2H), 6.75–6.95 (m, 2H), 5.1–5.25 (m, 1H), 3.85–4.0 (m, 2H), 3.1–3.85 (m, 51H), 0.6–1.8 (m, 115H).

Example 14

Preparation of
α-(4-N-Methylcarbamylbenzoyl)-ω-4-
dodecylphenoxypoly(oxybutylene)

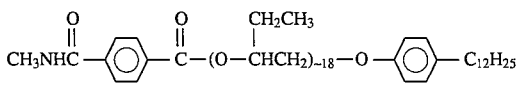

To a flask equipped with a magnetic stirrer, addition funnel and nitrogen inlet was added methylamine (2.2 mL of a 40 weight percent solution in water), tetrahydrofuran (75 mL), and α-(mono-terephthaloyl)-ω-4-dodecylphenoxypoly(oxybutylene) chloride (9.0 grams, prepared as in Example 11). The reaction was stirred at room temperature for 16 hours, diluted with diethyl ether (200·mL), washed twice with saturated aqueous sodium bicarbonate solution, and once with saturated aqueous sodium chloride. The organic layer was then dried over anhydrous magnesium sulfate, filtered and the solvents removed in vacuo. The oil was chromatographed on silica gel, eluting with hexane/diethyl ether/ethanol (70:29:1) to afford 6.5 grams of the desired product as an oil. The product had an average of 18 oxybutylene units. $^1$H NMR (CDCl$_3$) δ8.1, 7.8 (AB quartet, 4H), 7.1–7.25 (m, 2H), 6.75–6.95 (m, 2H), 6.55–6.75 (be, 1H), 5.1–5.25 (m, 1H), 3.85–4.0 (m, 2H), 3.1–3.85 (m, 51H), 3.0 (d, 3H), 0.6–1.8(m, 115 ).

Example 15

Preparation of
α-(4-N-N-Dimethylcarbamylbenzoyl)-ω-4-
dodecylphenoxypolyl(oxybutylene)

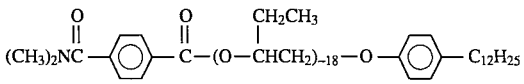

To a flask equipped with a magnetic stirrer, addition funnel and nitrogen inlet was added dimethylamine (4.2 mL of a 40 weight percent solution in water), tetrahydrofuran (75 mL), and α-(mono-terephthaloyl)-ω-4-dodecylphenoxypoly(oxybutylene) chloride (12.0 grams, prepared as in Example 11). The reaction was stirred at room temperature for 16 hours, diluted with diethyl ether (200 mL), washed twice with saturated aqueous sodium bicarbonate solution, and once with saturated aqueous sodium chloride. The organic layer was then dried over anhydrous magnesium sulfate, filtered and the solvents removed in vacuo. The oil was chromatographed on silica gel, eluting with hexane/diethyl ether/ethanol (70:29:1) to afford 10.2 grams of the desired product as an oil. The product had an average of 18 oxybutylene units. $^1$H NMR (CDCl$_3$) δ8.2, 7.5 (AB quartet, 4H), 7.1–7.25 (m, 2H), 6.75–6.95 (m, 2H), 5.1–5.25 (m, 1H), 3.85–4.0 (m, 2H), 3.1–3.85 (m, 51H), 3.1 (s, 3H), 2.95 (s, 3H), 0.6–1.8 (m, 115H).

Comparative Example A

Preparation of
α-(Benzoyl-ω-4-dodecylphenoxypolyl(oxybutylene)

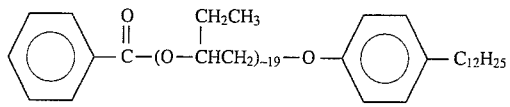

Benzoyl chloride (2.32 mL) was combined with 35.9 grams of α-hydroxy-ω-4-dodecylphenoxypoly(oxybutylene) having an average of 19 oxybutylene units (prepared essentially as described in Example 6 of U.S. Pat. No. 4,160,648) and 250 mL of anhydrous toluene. Triethylamine (3.1 mL) and 4-dimethylamino pyridine (1.22 grams) were then added and the resulting mixture was heated to reflux under nitrogen for 16 hours. The reaction was cooled to room temperature and diluted with 600 mL of diethyl ether. The organic layer was then washed with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 41.3 grams of a yellow oil. The oil was chromatographed on silica gel, eluting with hexane/diethyl ethyl/ethanol (70:25:5) to afford 29.0 grams of the desired product as a light yellow oil. The product had an average of 18 oxybutylene units. IR (neat) 1715 cm$^{-1}$; $^1$H NMR (CDCl$_3$) δ8.1 (d, 2H), 7.5–7.65 (m, 1H), 7.3–7.5 (m, 2H), 7.1–7.25 (m, 2H), 6.75–6.85 (m, 2H), 5.1–5.2 (m, 1H), 3.8–4.0 (m, 2H), 3.1–3.8 (m, 54H), 0.6–1.8 (m, 120H).

Example 16

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacketltemperature 200° F.; vacuum of 12 in Hg, air-fuel ratio of 12, ignition spark timing of 40° BTC; engine speed is 1800 rpm; the crankcase oil is a commercial 30 W oil.

The amount of carbonaceous deposit in milligrams on the intake valves is reported for each of the test compounds in Table I.

TABLE I

| Sample[1] | Intake Valve Deposit Weight (in milligrams) | | |
|---|---|---|---|
| | Run 1 | Run 2 | Average |
| Base Fuel | 168.0 | 179.2 | 173.6 |
| Example 3 | 46.6 | 70.7 | 58.7 |
| Example 4 | 25.1 | 24.1 | 24.6 |
| Example 5 | 78.4 | 108.4 | 93.4 |
| Example 6 | 82.9 | 93.9 | 88.4 |
| Example 7 | 46.3 | 64.0 | 55.2 |

TABLE I-continued

| Sample[1] | Intake Valve Deposit Weight (in milligrams) | | |
|---|---|---|---|
| | Run 1 | Run 2 | Average |
| Example 9 | 53.1 | 45.6 | 49.4 |
| Example 10 | 46.4 | 23.0 | 34.7 |
| Example 12 | 27.8 | 26.2 | 27.0 |
| Example 13 | 21.0 | 23.5 | 22.3 |
| Example 14 | 17.1 | 23.3 | 20.2 |
| Example 15 | 29.3 | 35.2 | 32.3 |
| Comp. Exam. A | 201.0 | 207.4 | 204.2 |

[1] At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by the polyalkyl and poly-(oxyalkylene) aromatic esters of the present invention (Examples 3–7, 9–10 and 12–15) compared to the base fuel and the poly(oxyalkylene) aromatic ester of Comparative Example A.

What is claimed is:

1. A compound of the formula:

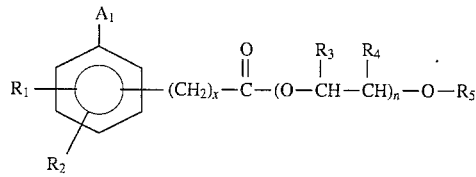

wherein $A_1$ is selected from the group consisting of $SR'$, $SOR''$, $SO_2R'''$, wherein $R'$, $R''$ and $R'''$ are independently lower alkyl of 1 to 6 carbon atoms; $SO_2NR^{IV}R^V$, wherein $R^{IV}$ and $R^V$ are independently hydrogen, lower alkyl of 1 to 6 carbon atoms or aminoalkyl of 1 to 6 carbon atoms, provided that $R^{IV}$ and $R^V$ may not both be aminoalkyl; CN; and $C(O)NR^{VII}R^{VIII}$, wherein $R^{VII}$ and $R^{VIII}$ are independently hydrogen, lower alkyl of 1 to 6 carbon atoms or aminoalkyl of 1 to 6 carbon atoms, provided that $R^{VII}$ and $R^{VIII}$ may not both be aminoalkyl;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—CHR$_3$—CHR$_4$— unit;

n is an integer from 0 to 100;

and when n is 0 to 10, then $R_5$ is a polyalkyl group having an average molecular weight in the range of about 450 to 5,000;

and when n is 5 to 100, then $R_5$ is hydrogen, alkyl having 1 to 100 carbon atoms, phenyl, aralkyl having 7 to 100 carbon atoms, alkaryl having 7 to 100 carbon atoms, or an acyl group having the formula:

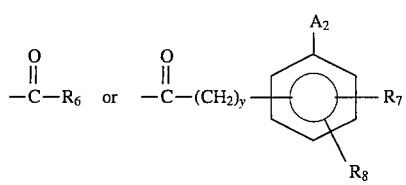

wherein $R_6$ is alkyl having 1 to 30 carbon atoms, phenyl, aralkyl having 7 to 36 carbon atoms or alkaryl having 7 to 36 carbon atoms;

$R_7$ and $R_8$ are independently hydrogen, hydroxy, lower alkyl having 1 to 6 carbon atoms, or lower alkoxy having 1 to 6 carbon atoms;

$A_2$ is selected from the group consisting of $SR^{IX}$, $SOR^X$, $SO_2R^{XI}$, wherein $R^{IX}$, $R^X$ and $R^{XI}$ are independently lower alkyl of 1 to 6 carbon atoms; $SO_2NR^{XII}R^{XIII}$, wherein $R^{XII}$ and $R^{XIII}$ are independently hydrogen or lower alkyl of 1 to 6 carbon atoms; CN; and $C(O)NR^{XV}R^{XVI}$, wherein $R^{XV}$ and $R^{XVI}$ are independently hydrogen or lower alkyl of 1 to 6 carbon atoms;

and x and y are independently integers from 0 to 10;

with the proviso that when n and x are both 0, then $A_1$ may not be $C(O)NR^{VII}R^{VIII}$.

2. The compound according to claim 1 wherein $R_1$ is hydrogen, hydroxy or lower alkyl having 1 to 4 carbon atoms.

3. The compound according to claim 2 wherein $R_1$ is hydrogen or hydroxy.

4. The compound according to claim 3 wherein $R_1$ is hydrogen.

5. The compound according to claim 1 wherein $R_2$ is hydrogen.

6. The compound according to claim 1 wherein x is an integer from 0 to 2.

7. The compound according to claim 6 wherein x is 0.

8. The compound according to claim 1 wherein n is an integer from 0 to 10.

9. The compound according to claim 8 wherein n is an integer from 0 to 5.

10. The compound according to claim 9 wherein n is 0.

11. The compound according to claim 8 wherein $R_1$ and $R_2$ are both hydrogen and x and n are both 0.

12. The compound according to claim 8 wherein $R_5$ is a polyalkyl group derived from polypropylene, polybutene, or polyalphaolefin oligomers of 1-octene or 1-decene.

13. The compound according to claim 12 wherein $R_5$ is a polyalkyl group derived from polyisobutene.

14. The compound according to claim 1 wherein n is an integer from 5 to 100.

15. The compound according to claim 14 wherein n is an integer from 8 to 50.

16. The compound according to claim 15 wherein n is an integer from 10 to 30.

17. The compound according to claim 14 wherein $R_5$ is hydrogen, alkyl having 1 to 30 carbon atoms or alkylphenyl having an alkyl group containing 1 to 30 carbon atoms.

18. The compound according to claim 1 wherein one of $R_3$ and $R_4$ is lower alkyl having 1 to 3 carbon atoms and the other is hydrogen.

19. The compound according to claim 18 wherein one of $R_3$ and $R_4$ is methyl or ethyl and the other is hydrogen.

20. The compound according to claim 14 wherein $R_1$ and $R_2$ are hydrogen, $R_5$ is alkylphenyl having an alkyl group containing 4 to 12 carbon atoms, and x is 0.

21. The compound according to claim 1 wherein $A_1$ is selected from the group consisting of $SR^I$, $SO_2R^{III}$, CN, and $C(O))NR^{VII}R^{VIII}$.

22. The compound according to claim 21 wherein $A_1$ is $C(O)NR^{VII}R^{VIII}$.

23. A fuel composition comprising a major amount of hydrocarbons boiling in the gasoline or diesel range and an effective detergent amount of a compound of the formula:

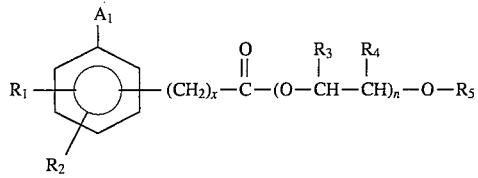

wherein $A_1$ is selected from the group consisting of $SR^I$, $SOR^{II}$, $SO_2R^{III}$, wherein $R^I$, $R^{II}$ and $R^{III}$ are independently lower alkyl of 1 to 6 carbon atoms; $SO_3H$; $SO_2NR^{IV}R^V$, wherein $R^{IV}$ and $R^V$ are independently hydrogen, lower alkyl of 1 to 6 carbon atoms or aminoalkyl of 1 to 6 carbon atoms, provided that $R^{IV}$ and $R^V$ may not both be aminoalkyl; CN; $CO_2R^{VI}$, wherein $R^{VI}$ is hydrogen or lower alkyl of 1 to 6 carbon atoms; and $C(O)NR^{VII}R^{VIII}$, wherein $R^{VII}$ and $R^{VIII}$ are independently hydrogen, lower alkyl of 1 to 6 carbon atoms or aminoalkyl of 1 to 6 carbon atoms, provided that $R^{VII}$ and $R^{VIII}$ may not both be aminoalkyl;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each $-O-CHR_3-CHR_4-$ unit;

n is an integer from 0 to 100;

and when n is 0 to 10, then $R_5$ is a polyalkyl group having an average molecular weight in the range of about 450 to 5,000;

and when n is 5 to 100, then $R_5$ is hydrogen, alkyl having 1 to 100 carbon atoms, phenyl, aralkyl having 7 to 100 carbon atoms, alkaryl having 7 to 100 carbon atoms, or an acyl group having the formula:

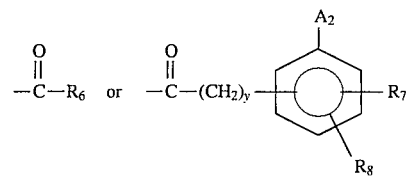

wherein $R_6$ is alkyl having 1 to 30 carbon atoms, phenyl, aralkyl having 7 to 36 carbon atoms or alkaryl having 7 to 36 carbon atoms;

$R_7$ and $R_8$ are independently hydrogen, hydroxy, lower alkyl having 1 to 6 carbon atoms, or lower alkoxy having 1 to 6 carbon atoms;

$A_2$ is selected from the group consisting of $SR^{IX}$, $SOR^X$, $SO_2R^{XI}$, wherein $R^{IX}$, $R^X$ and $R^{XI}$ are independently lower alkyl of 1 to 6 carbon atoms; $SO_3H$; $SO_2NR^{XII}R^{XIII}$, wherein $R^{XII}$ and $R^{XIII}$ are independently hydrogen or lower alkyl of 1 to 6 carbon atoms; CN; $CO_2R^{XIV}$, wherein $R^{XIV}$ is hydrogen or lower alkyl of 1 to 6 carbon atoms; and $C(O)NR^{XV}R^{XVI}$, wherein $R^{XV}$ and $R^{XVI}$ are independently hydrogen or lower alkyl of 1 to 6 carbon atoms;

and x and y are independently integers from 0 to 10;

with the proviso that when n and x are both 0, then $A_1$ may not be $CO_2R^{VI}$ or $C(O)NR^{VII}R^{VIII}$.

24. The fuel composition according to claim 23 wherein $R_1$ is hydrogen, hydroxy or lower alkyl having 1 to 4 carbon atoms.

25. The fuel composition according to claim 24 wherein $R_1$ is hydrogen or hydroxy.

26. The fuel composition according to claim 25 wherein $R_1$ is hydrogen.

27. The fuel composition according to claim 23 wherein $R_2$ is hydrogen.

28. The fuel composition according to claim 23 wherein x is an integer from 0 to 2.

29. The fuel composition according to claim 28 wherein x is 0.

30. The fuel composition according to claim 23 wherein n is an integer from 0 to 10.

31. The fuel composition according to claim 30 wherein n is an integer from 0 to 5.

32. The fuel composition according to claim 31 wherein n is 0.

33. The fuel composition according to claim 30 wherein $R_1$ and $R_2$ are both hydrogen and x and n are both 0.

34. The fuel composition according to claim 30 wherein $R_5$ is a polyalkyl group derived from polypropylene, polybutene, or polyalphaolefin oligomers of 1-octene or 1-decene.

35. The fuel composition according to claim 34 wherein $R_5$ is a polyalkyl group derived from polyisobutene.

36. The fuel composition according to claim 23 wherein n is an integer from 5 to 100.

37. The fuel composition according to claim 36 wherein n is an integer from 8 to 50.

38. The fuel composition according to claim 37 wherein n is an integer from 10 to 30.

39. The fuel composition according to claim 36 wherein $R_5$ is hydrogen, alkyl having 1 to 30 carbon atoms or alkylphenyl having an alkyl group containing 1 to 30 carbon atoms.

40. The fuel composition according to claim 23 wherein one of $R_3$ and $R_4$ is lower alkyl having 1 to 3 carbon atoms and the other is hydrogen.

41. The fuel composition according to claim 40 wherein one of $R_3$ and $R_4$ is methyl or ethyl and the other is hydrogen.

42. The fuel composition according to claim 36 wherein $R_1$ and $R_2$ are hydrogen, $R_5$ is alkylphenyl having an alkyl group containing 4 to 12 carbon atoms, and x is 0.

43. The fuel composition according to claim 23 wherein $A_1$ is selected from the group consisting of $SR^I$, $SO_2R^{III}$, CN, $CO_2R^{VI}$ and $C(O)NR^{VII}R^{VIII}$.

44. The fuel composition according to claim 43 wherein $A_1$ is $CO_2R^{VI}$ or $C(O)NR^{VII}R^{VIII}$.

45. A fuel concentrate comprising an inert stable oleophilic organic solvent boiling in the range of from about 150° F. to 400° F. and from about 10 to about 70 weight percent of a compound of the formula:

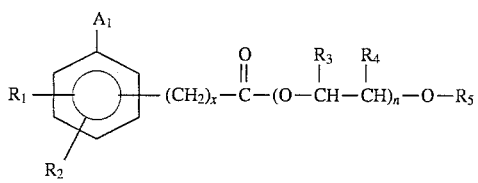

wherein $A_1$ is selected from the group consisting of $SR^I$, $SOR^{II}$, $SO_2R^{III}$, wherein $R^I$, $R^{II}$ and $R^{III}$ are independently lower alkyl of 1 to 6 carbon atoms; $SO_3H$; $SO_2NR^{IV}R^V$, wherein $R^{IV}$ and $R^V$ are independently hydrogen, lower alkyl of 1 to 6 carbon atoms or aminoalkyl of 1 to 6 carbon atoms, provided that $R^{IV}$ and $R^V$ may not both be aminoalkyl; CN; $CO_2R^{VI}$, wherein $R^{VI}$ is hydrogen or lower alkyl of 1 to 6 carbon atoms; and $C(O)NR^{VII}R^{VIII}$, wherein $R^{VII}$ and $R^{VIII}$ are independently hydrogen, lower alkyl of 1 to 6 carbon atoms or aminoalkyl of 1 to 6 carbon atoms, provided that $R^{VII}$ and $R^{VIII}$ may not both be aminoalkyl;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—$CHR_3$—$CHR_4$— unit;

n is an integer from 0 to 100;

and when n is 0 to 10, then $R_5$ is a polyalkyl group having an average molecular weight in the range of about 450 to 5,000;

and when n is 5 to 100, then $R_5$ is hydrogen, alkyl having 1 to 100 carbon atoms, phenyl, aralkyl having 7 to 100 carbon atoms, alkaryl having 7 to 100 carbon atoms, or an acyl group having the formula:

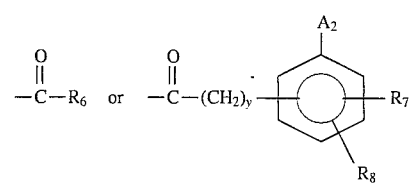

wherein $R_6$ is alkyl having 1 to 30 carbon atoms, phenyl, aralkyl having 7 to 36 carbon atoms or alkaryl having 7 to 36 carbon atoms;

$R_7$ and $R_8$ are independently hydrogen, hydroxy, lower alkyl having 1 to 6 carbon atoms, or lower alkoxy having 1 to 6 carbon atoms;

$A_2$ is selected from the group consisting of $SR^{IX}$, $SOR^X$, $SO_2R^{XI}$, wherein $R^{IX}$, $R^X$ and $R^{XI}$ are independently lower alkyl of 1 to 6 carbon atoms; $SO_3H$; $SO_2NR^{XII}R^{XIII}$, wherein $R^{XII}$ and $R^{XIII}$ are independently hydrogen or lower alkyl of 1 to 6 carbon atoms; CN; $CO_2R^{XIV}$, wherein $R^{XIV}$ is hydrogen or lower alkyl of 1 to 6 carbon atoms; and $C(O)NR^{XV}R^{XVI}$, wherein $R^{XV}$ and $R^{XVI}$ are independently hydrogen or lower alkyl of 1 to 6 carbon atoms;

and x and y are independently integers from 0 to 10;

with the proviso that when n and x are both 0, then $A_1$ may not be $CO_2R^{VI}$ or $C(O)NR^{VII}R^{VIII}$.

46. The fuel concentrate according to claim 45 wherein $R_1$ is hydrogen, hydroxy or lower alkyl having 1 to 4 carbon atoms.

47. The fuel concentrate according to claim 46 wherein $R_1$ is hydrogen or hydroxy.

48. The fuel concentrate according to claim 47 wherein $R_1$ is hydrogen.

49. The fuel concentrate according to claim 45 wherein $R_2$ is hydrogen.

50. The fuel concentrate according to claim 45 wherein x is an integer from 0 to 2.

51. The fuel concentrate according to claim 50 wherein x is 0.

52. The fuel concentrate according to claim 46 wherein n is an integer from 0 to 10.

53. The fuel concentrate according to claim 52 wherein n is an integer from 0 to 5.

54. The fuel concentrate according to claim 53 wherein n is 0.

55. The fuel concentrate according to claim 52 wherein $R_1$ and $R_2$ are both hydrogen and x and n are both 0.

56. The fuel concentrate according to claim 52 wherein $R_5$ is a polyalkyl group derived from polypropylene, polybutene, or polyaiphaolefin oligomers of 1-octene or 1-decene.

57. The fuel concentrate according to claim 56 wherein $R_5$ is a polyalkyl group derived from polyisobutene.

58. The fuel concentrate according to claim 45 wherein n is an integer from 5 to 100.

59. The fuel concentrate according to claim 58 wherein n is an integer from 8 to 50.

60. The fuel concentrate according to claim 59 wherein n is an integer from 10 to 30.

61. The fuel concentrate according to claim 58 wherein $R_5$ is hydrogen, alkyl having 1 to 30 carbon atoms or alkylphenyl having an alkyl group containing 1 to 30 carbon atoms.

62. The fuel concentrate according to claim 45 wherein one of $R_3$ and $R_4$ is lower alkyl having 1 to 3 carbon atoms and the other is hydrogen.

63. The fuel concentrate according to claim 62 wherein one of $R_3$ and $R_4$ is methyl or ethyl and the other is hydrogen.

64. The fuel concentrate according to claim 58 wherein $R_1$ and $R_2$ are hydrogen, $R_5$ is alkylphenyl having an alkyl group containing 4 to 12 carbon atoms, and x is 0.

65. The fuel concentrate according to claim 45 wherein $A_1$ is selected from the group consisting of $SR^I$, $SO_2R^{III}$, CN, $CO_2R^{VI}$ and $C(O)NR^{VII}R^{VIII}$.

66. The fuel concentrate according to claim 65 wherein $A_1$ is $CO_2R^{VI}$ or $C(O)NR^{VII}R^{VIII}$.

* * * * *